United States Patent [19]

Lartigau et al.

[11] 3,968,162

[45] July 6, 1976

[54] PREPARATION OF ACETOPHENONE

[75] Inventors: Guy Lartigau, Tassin-la-demi-Lune; Pierre-Etienne Bost, Paris, both of France

[73] Assignee: Rhone-Poulenc S.A., Paris, France

[22] Filed: May 24, 1974

[21] Appl. No.: 473,268

[30] Foreign Application Priority Data

May 28, 1973 France .............................. 73.19289

[52] U.S. Cl. ............................ 260/592; 260/632 R; 252/476
[51] Int. Cl.² ......................................... C07C 49/78
[58] Field of Search ..................................... 260/592

[56] References Cited

UNITED STATES PATENTS

| | | | |
|---|---|---|---|
| 2,557,968 | 6/1951 | Hulse et al. | 260/592 |
| 3,154,586 | 10/1964 | Bander et al. | 260/597 B |
| 3,365,498 | 1/1968 | Bryant et al. | 260/597 B |

*Primary Examiner*—James O. Thomas, Jr.
*Assistant Examiner*—James H. Reamer
*Attorney, Agent, or Firm*—Cushman, Darby & Cushman

[57] ABSTRACT

Acetophenone is made by decomposing cumene hydroperoxide in a mixture of water, a copper catalyst, and α-methylstyrene or dimethylphenylcarbinol.

6 Claims, No Drawings

PREPARATION OF ACETOPHENONE

The present invention relates to the catalytic decomposition of cumene hydroperoxide to yield acetophenone.

According to the present invention, cumene hydroperoxide is decomposed to yield acetophenone in a reaction medium containing water, a copper-containing catalyst and α-methylstyrene or dimethylphenylcarbinol.

The quantities of water and the hydroperoxide in the reaction medium are generally such that the ratio by weight of the hydroperoxide to water is between $10^{-4}$ and 10, and preferably between 0.01 and 0.3.

An inorganic or organic derivative of copper may be used as the catalyst, but an organic or inorganic cupric or cuprous salt is generally used. It is preferred to use copper (usually cupric) salts of strong inorganic acids and especially the nitrate, sulphate, perchlorate or a halide, e.g. the chloride or bromide. Suitable organic acid salts include the acetate, propionate and butyrate.

Other copper compounds can be used, especially if, under the working conditions chosen, they are converted into one of the preferred derivatives just mentioned.

The quantity of copper catalyst employed is usually such that the ratio of the number of mols of the hydroperoxide in the reaction mixture to the number of gram atoms of copper dissolved in the aqueous phase is between 5 and $10^4$, and preferably between 10 and $10^3$. By "aqueous phase" is meant either the single phase of the reaction mixture if the latter is homogeneous, or, if the latter is heterogeneous, the phase which has the maximum water content.

α-Methylstyrene or dimethylphenylcarbinol is used in a weight which is generally 0.1 to 4 times (in mols) the weight of cumene hydroperoxide, and preferably between 0.5 and 2 times.

The reaction temperature is usually between 50° and 150°C., and preferably between 80° and 120°C.

The new process makes it possible to obtain good yields of acetophenone under relatively mild conditions. It also makes it possible to obtain methanol in substantial quantities as a by-product.

The following Examples illustrate the invention.

EXAMPLES 1 TO 6

The following general procedure was used.

5 millimols of the catalyst, 100 cm³ of water and the α-methylstyrene or dimethylphenylcarbinol are introduced successively into a glass flask equipped with a stirrer and a reflux condenser. The mixture is heated to reflux temperature (approximately 98°C.) and 0.1 mol of cumene hydroperoxide in then run in. The mixture is kept under reflux for a period of time t. At the end of the reaction, the reaction mixture is cooled and extracted with benzene, and the products formed are measured.

The Table below gives the working conditions and the results obtained for the various Examples. The degree of conversion of cumene hydroperoxide is practically 100 percent in every case. The yield of acetophenone is calculated relative to the cumene hydroperoxide introduced.

TABLE

| Example | Catalyst | α-methylstyrene (mols) | | dimethylphenyl-carbinol (mols) | | duration t (minutes) | yield of acetophenone (%) |
|---|---|---|---|---|---|---|---|
| | | introduced | recovered | introduced | recovered | | |
| 1 | $CuSO_4.5H_2O$ | 0 | | 0.1 | 0.115 | 180 | 83 |
| 2 | $CuSO_4.5H_2O$ | 0 | | 0.05 | 0.068 | 190 | 70 |
| 3 | $CuSO_4.5H_2O$ | 0 | | 0.2 | 0.185 | 195 | 89.5 |
| 4 | $Cu(OCOCH_3)_2.H_2O$ | 0 | | 0.2 | 0.2 | 240 | 65.6 |
| 5 | $CuSO_4.5H_2O$ | 0.2 | 0.19 | 0 | | 150 | 89.5 |
| 6 | $CuSO_4.5H_2O$ | 0.1 | 0.083 | 0 | | 120 | 91 |

We claim:

1. Process for the production of acetophenone which comprises decomposing cumene hydroperoxide in a reaction medium containing water, a water-soluble cupric salt as catalyst, and alpha-methylstyrene or dimethylphenylcarbinol, the ratio of the number of mols of the hydroperoxide to the number of gram atoms of copper in the aqueous phase being between 5 and $10^4$, the weight of alpha-methylstyrene or dimethylphenylcarbinol being 0.1 to 4 times in mols the weight of the hydroperoxide.

2. Process according to claim 1 in which the said ratio is between 10 and $10^3$.

3. Process according to claim 1 in which the temperature of the decomposition is 50° to 150°C.

4. Process according to claim 1 in which the ratio by weight of the hydroperoxide to the water is between $10^{-4}$ and 10.

5. Process according to claim 4 in which the said ratio is between 0.01 and 0.3.

6. Process according to claim 1 in which the copper-containing catalyst is cupric sulphate, cupric nitrate, cupric perchlorate, cupric chloride, cupric bromide, cupric acetate, cupric propionate, or cupric butyrate.

* * * * *